United States Patent [19]

Kalend et al.

[11] Patent Number: 5,784,431
[45] Date of Patent: Jul. 21, 1998

[54] APPARATUS FOR MATCHING X-RAY IMAGES WITH REFERENCE IMAGES

[75] Inventors: Andre M. Kalend, Monroeville; Joel Greenberger, Sewickley; Karun B. Shimoga, Pittsburgh, all of Pa.; Charalambos N. Athanassiou, Athens, Greece; Takeo Kanade, Pittsburgh, Pa.

[73] Assignee: University of Pittsburgh of the Commonwealth System of Higher Education, Pittsburgh, Pa.

[21] Appl. No.: 739,622

[22] Filed: Oct. 29, 1996

[51] Int. Cl.$^6$ .................................................. A61N 5/10
[52] U.S. Cl. ............................ 378/65; 378/69; 378/901
[58] Field of Search ................................. 378/8, 20, 65, 378/68, 69, 901

[56] References Cited

U.S. PATENT DOCUMENTS

| | | | |
|---|---|---|---|
| 4,995,068 | 2/1991 | Chou et al. | 378/189 |
| 5,315,630 | 5/1994 | Strum et al. | 378/65 |
| 5,398,684 | 3/1995 | Hardy | 128/653.1 |

OTHER PUBLICATIONS

IEEE Transactions on Pattern Analysis and Machine Intelligence, vol. PAMI-7, No. 3, *Template Matching in Rotated Images*, A. Goshtasby, pp. 338-344, May 1985.

*Image Registration by Local Approximation Methods*, vol. 6, No. 4, A. Goshtasby, pp. 255-261, Nov. 1988.

Computer Vision, Graphics, and Image Processing 47, *Automated Registration of Dissimilar Images: Application to Medical Imagery*, M. Herbin et al., pp. 77-88, 1989.

Computer and Robot Vision, vol. I, 7.2.12 *Noise-Removal Techniques-Experiments*, R. Haralick and L. Shapiro, 1992.

International Journal of Computer Vision, 8:2, 99-111, *Feature Extraction from Faces Using Deformable Templates*, A. Yuille et al., pp. 99-111, 1992.

*Pseudocorrelation: A fast, robust, absolute, grey-level image alignment algorithm*, Medical Physics, vol. 21, No. 6, R. Radcliffe et al., pp. 761-769, Jun., 1994.

Technical paper of Xerox Palo Alto Research Center, *Tracking and Recognizing Facial Expressions in Image Sequences, using Local Parameterized Models of Image Motion*, M. Black and Y. Yacoob, Jan. 1995.

*Clinical implementation of an objective computer-aided protocol for intervention in intra-treatment correction using electronic portal imaging*, F. Van den Heuvel et al., Radiotherapy and Oncology 35 (1995) 232-239, Jun. 1995.

*A Framework for the Robust Estimation of Optical Flow*, Black, Michael J., Proc. Fourth Int. Conf. on Computer Vision (ICCV'93), Berlin, Germany May 1993.

*Primary Examiner*—David P. Porta
*Assistant Examiner*—David Vernon Bruce
*Attorney, Agent, or Firm*—Richard V. Westerhoff; Eckert Seamans Cherin & Mellot, LLC

[57] ABSTRACT

X-ray images such as radiotherapy portal images and simulation images are matched by apparatus which digitizes the images and automatically processes the digitized signals to generate matched digitized signals which can be displayed for comparison. The digitized images are first coarse aligned using a transform generated from seed points selected interactively from the two images or through detection and identification of x-ray opaque fiducials placed on the patient. A fine alignment is then performed by first selecting intersecting regions of the two images and enhancing those regions. Secondly, an updated transform is generated using robust motion flow in these regions at successive ascending levels of resolution. The updated transform is then used to align the images which are displayed for comparison. The updated transform can also be used to control the radiotherapy equipment.

28 Claims, 8 Drawing Sheets

APPARATUS FOR MATCHING X-RAY IMAGES WITH REFERENCE IMAGES

BACKGROUND OF THE INVENTION

1. Field of the Invention

This invention relates to matching similar x-ray images and has particular application to computer controlled radiotherapy apparatus for automatically matching on-line the portal images generated during radiotherapy treatment on a treatment machine with simulation images generated prior to treatment on a simulation machine for determining that the desired target is actually being irradiated for the purposes of assessment, and/or controlling the treatment equipment.

2. Background Information

There are medical applications which require matching of x-ray images. For instance, in computer controlled radiotherapy, treatment beams of high energy radiation are directed at a tumor from a number of directions so as to maximize irradiation of the tumor while minimizing exposure of healthy tissue surrounding the tumor. Such radiotherapy treatment typically has two distinct phases: the simulation phase, and the actual treatment phase. In the simulation phase, the patient is placed on equipment similar to the treatment equipment except that it does not generate the high energy radiation beam. The simulation equipment is successively positioned to simulate the delivery of the sequence of treatment beams prescribed by the treating oncologist. This assures that the equipment can be positioned to deliver the required treatment beams and progressively move from one treatment beam to the next without collision between the equipment and the patient or between movable components of the equipment. During this procedure a low dosage x-ray image called the simulation image is taken. This simulation image, which generally has good contrast and detail because of the low energy of the x-ray beam used (in the kiloelectronvolt range) helps the oncologist to locate the position of the tumor and thereby establish the positions of the equipment components for delivering the successive treatment beams.

During the actual treatment phase, the patient is placed in the exact same position on the equipment as in the simulation before the regular-dosage x-ray radiation, typically in the megaelectronvolt range, is used to treat the patient. During this phase, another x-ray image is taken, which is called the portal image.

After completion of the treatment, the simulation and portal images are compared by an expert to determine whether the tumor, as identified in the simulation image, has been adequately treated with radiation in the portal image. If the coverage is not complete, the patient is scheduled for a corrective treatment.

The current accepted procedure involves the manual comparison of the portal and simulation images. Accurate manual comparison is quite challenging given the fact that the two x-rays are usually taken by different equipment and at different levels of radiation exposure. The latter fact implies that the tumor area is usually not visible in the portal x-ray, and thus the matching of the portal image with that of the simulation has to rely on manual estimation of dimensions from anatomical landmarks, which will not be clearly visible.

Conventionally, the portal images have been generated by using x-ray film which has to be developed. This is not a serious drawback where only a single or a few treatment beams are utilized. However, this x-ray film is a serious limitation in computer controlled radiotherapy where a large number of treatment beams are used. Electronic portal imagers have been developed which generate a digitized image which can be displayed on an electronic display device. Unfortunately, the same problems exist as to the contrast and definition in the portal image generated electronically.

The problem of matching portal images with simulation images is compounded by the fact that the images have differences in orientation caused by skewing, scaling differences, rotation, translation and differences in perspective and curvature.

In stereotactic radiology, digitized computed tomography x-ray images and magnetic resonance images (MRI) have been automatically matched by applying scaling derived from known fixed dimensions of a steel frame which appears in both images. Such fixed landmarks of known dimensions are not available in conventional radiotherapy images.

There is a need, therefore, for apparatus for automatically matching x-ray images and particularly for matching portal images with simulation images in radiotherapy.

There is also a need for such apparatus which can match the portal and simulation images on-line for multiple treatment beams.

There is further need for such apparatus which can match portal images and simulation images having widely different contrast and definition and differences caused by skewing, rotation, scaling, perspective or curvature.

There is an additional need for apparatus for obtaining and maintaining alignment of a patient during computed controlled radiotherapy or for terminating the radiation beam if alignment becomes unacceptable.

SUMMARY OF THE INVENTION

These needs and others are satisfied by the invention which is directed to apparatus for automatically matching an x-ray image with a reference image, and particularly for matching the portal image with a simulation image for determining whether radiotherapy treatment has been adequate or for matching successive portal images for controlling operation of the radiotherapy equipment. In matching images, digitizing means digitizes the x-ray image such as the portal image to generate a first set of digital image signals or digital portal image signals (DPIS) in the case of the portal image. The digitizing means also digitizes the reference image such as the simulation image to generate second digital image signals or digital simulation signals (DSIS). Processing means process these digital image signals to generate matched digital image signals. The processing is performed without any prior knowledge of the physical dimensions of any of the features in the images. Output means generate for instance a display from the matched digital image signals and/or control the treatment/diagnosis equipment.

The processing means includes coarse alignment means which first effect a coarse alignment between the digital portal image signals and the digital simulation image signals. Coarse alignment is initiated by selecting seed points in the portal image represented by the DPIS and in the simulation image represented by the DSIS. Selection of the seed points can be done either interactively using a pointing device such as a mouse to select what appear to be corresponding points on displays of the two images, or automatically through use of x-ray opaque fiducials placed on the patient. In either case, the seed points are used to compute a transform between the two images. Means are then used to apply the transform to one of the sets of digital image signals to transform points in that image to the coordinates of the other image thereby producing coarse aligned DPIS and DSIS.

Following coarse alignment, a fine alignment is performed. In implementing the fine alignment, the coarse aligned DPIS and DSIS are first prepared by selecting selected DPIS and selected DSIS for regions of the images which intersect or overlap, and preferably for a region of regular shape such as a rectangle within the intersecting regions of the images. The digital image signals for these regions are then enhanced to produce prepared images with similar dynamic range and pixel intensities. The fine alignment means includes means generating an updated transform from the prepared DPIS and DSIS, and means applying the updated transform to either the coarse or prepared DPIS and DSIS to generate the matched DPIS and DSIS.

The means generating the updated transform comprises means generating motion flow components from the prepared DPIS and DSIS and calculating means calculating the updated transform from the motion flow components. Preferably the means generating the motion flow components generates motion flow gradient components and the calculating means comprises means applying a robust optimization to calculate the updated transform. The means generating updated transform uses successive ascending levels of resolution of the prepared DPIS and DSIS to generate the updated transform.

In the tracking mode, the updated transform is used to track movement between successive sets of digital portal image signals. Tracking can be used to terminate the radiation if patient movement exceeds specified limits, or could be used to operate the patient positioning assembly to maintain the radiation beam in proper alignment with the area to be treated.

The invention can also be used to match x-ray images with other reference images which could be another x-ray image or another type of image.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENT

The invention is directed to matching x-ray images with reference images and will be described as applied to matching portal images generated in computer controlled radiotherapy with simulation images. However, it will be understood that the invention has wide application in matching other x-ray images such as those used in diagnosis, for example. As will be seen, the invention also has application for tracking motion in successive portal images such as for controlling positioning of a patient or gating of the radiation beam.

Figure 1:
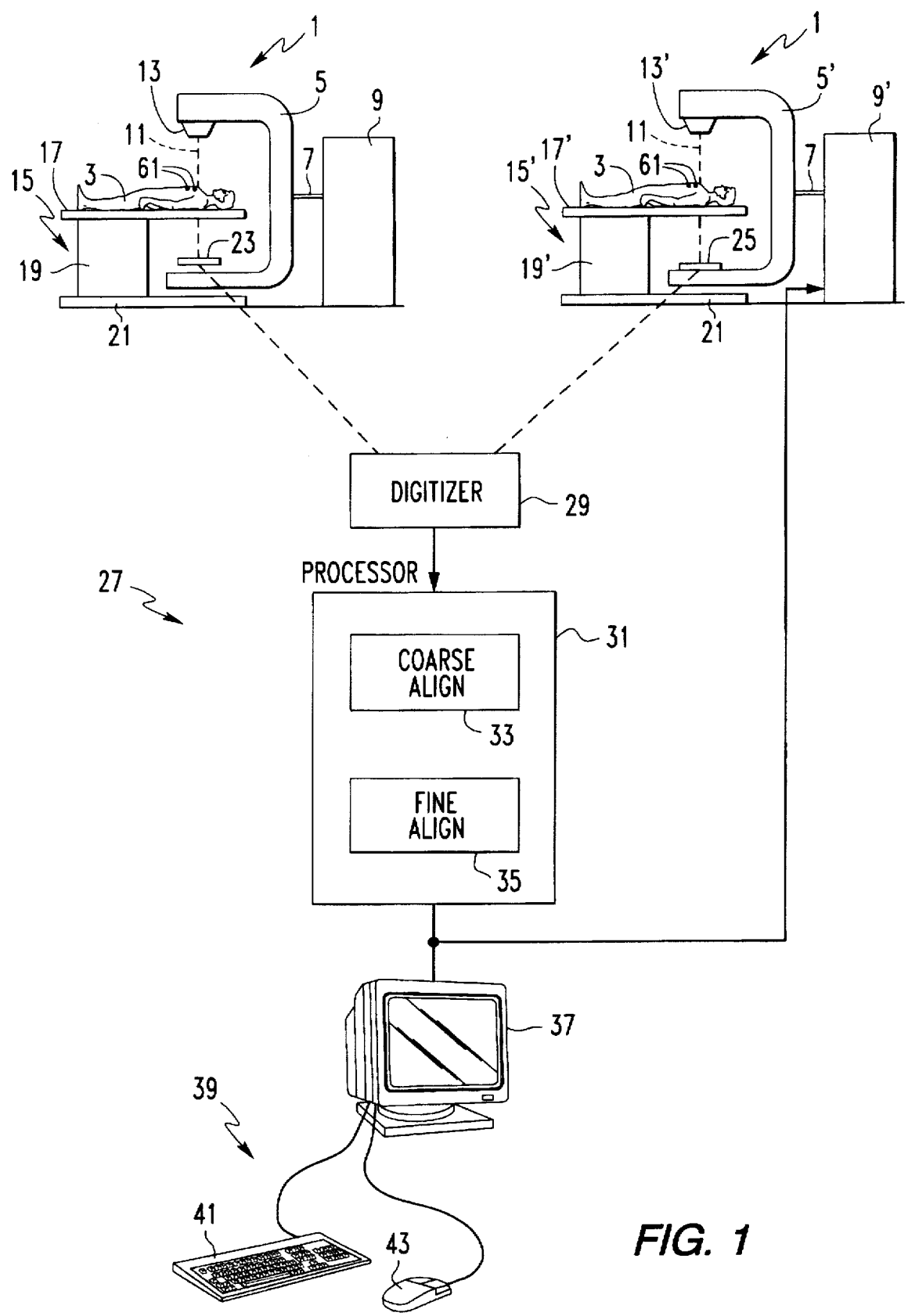
FIG. 1 is a schematic diagram of apparatus for implementing the invention.

Referring to FIG. 1, a simulation setup 1 is used for determining the location of the region such as a tumor within a patient 3 to be treated and for setting up the sequence of treatment beams. The setup equipment includes a gantry 5 mounted for rotation about a horizontal pivot 7 supported by a machine base 9. A low energy, in the kiloelectronvolt range, x-ray beam 11 is directed by a collimator 13 mounted on the gantry 5 along a path which extends transversely through an extension of the pivot 7.

The patient 3 is supported on a patient positioning assembly 15 which includes a couch 17 mounted on a support 19 for three dimensional translation relative to the support. The support 19, in turn, is mounted on a turntable 21. Through translation of the couch 17, rotation of the turntable 21 and rotation of the gantry 5 about the pivot 7, a plurality of treatment beams can be simulated. By sequencing the simulation equipment 1 through the positions required to generate the successive beams, it can be determined whether all of the required beams can be achieved and whether sequencing the movement of the equipment between beams must be adjusted to avoid collisions between the equipment and the patient or between components of the equipment.

The low energy x-ray beam 11 is used to generate simulation images by placement of an x-ray film 23 in line with the x-ray beam 11 on the other side of the patient 3 from the collimator 13. This simulation image is used to position the area of the patient to be treated, such as a tumor, at the isocenter of the setup, which is the intersection of the beam 11 with a projection of the pivot axis 7.

Following completion of the simulation, the patient 3 is transferred to the treatment setup 1'. As shown, the treatment setup at 1' is similar to the simulation setup 1, except that the x-ray beam 11' is in the megaelectronvolt range. A portal image is generated by the treatment setup 1'. This portal image can be captured by an x-ray film as in the simulation setup; however, it is preferred that an electronic portal imager 25 be used. If available, an electronic imager could also be used in place of the x-ray film 23 in the simulation setup 1.

As discussed above, the simulation image and the portal image can be quite different. One of the main reasons for this is the difference in the energy of the beams 11 and 11'. The invention can be used to match the simulation and portal images to determine if the treatment dosage was delivered to the proper treatment area. It can also be used to detect patient movement during treatment to terminate generation of the x-ray beam 11' if a movement exceeds proper limits, or to maneuver the equipment to maintain proper alignment.

The image matching system 27 includes a digitizer 29 which digitizes the simulation image such as produced on the x-ray film 23 and the portal image such as that generated by the electronic portal imager 25. In a more general sense, the matching system 27 matches an x-ray image, such as the portal image, with a reference image such as the simulation image.

The image matching system 27 further includes a processor 31 which includes a module for coarse alignment 33 followed by a module for fine alignment 35. The output of the processor can be matched portal (x-ray) and simulation (reference) images which are displayed on a display device 37. Associated with the display device 37 are interface devices 39 which can include a keyboard 41 and a pointing device 43, such as a mouse or a trackball.

Figure 2A:
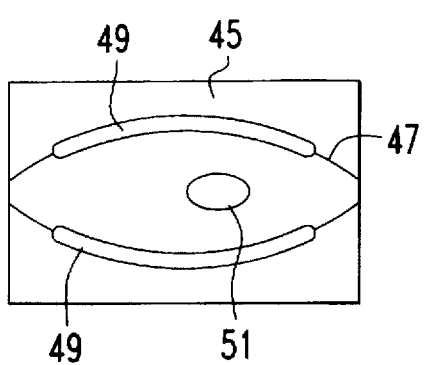
FIG. 2a is a simplified illustration of a simulation image to which the invention can applied.
Figure 2B:
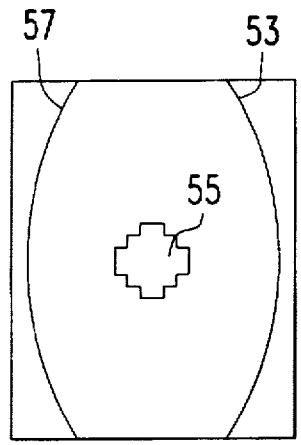
FIG. 2b is a simplified illustration of a portal image to which the invention may be applied.
Figure 2C:
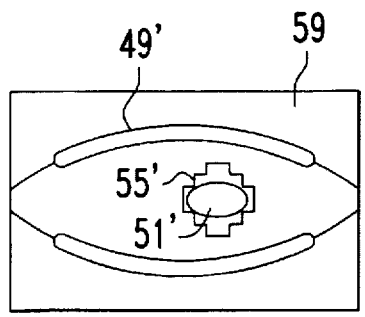
FIG. 2c is a simplified illustration of a display superimposing the simulation and portal images of FIGS. 2a and 2b utilizing the invention.

FIGS. 2a–2c illustrate that the invention can be used to match a portal x-ray image with a simulation reference image. FIG. 2a represents a simulation image 45 generated using the simulation setup 1. The low energy x-rays used for this image produce an image with good contrast and detail, so that the outline 47 of the patient and bony structure 49 are shown as well as the tumor 51. FIG. 2b illustrates the portal image which being taken with the higher energy treatment beam shows the treated area 55 as a uniform dark spot. The irregular edge of the treated area 55 is produced by the leaves used in the collimator 13 to conform the beam 11' generally to the shape of the tumor. The remainder of the portal image 55 shows little detail and does not indicate the location of the bones. As can be seen, the two images 45 and 53 can be translated relative to each other, scaled differently, skewed and rotated (by 90° in the example). The two images can also be different in perspective and in curvature.

The coarse alignment module 33 produces a general alignment of the two images, and then the fine alignment module 35 uses robust motion flow to rapidly and accurately complete matching of the images. The display device 37 can present the matched images in different ways. In one embodiment, the display 37 alternates between the two images at about 6 to 20 Hz, but usually about 12 Hz, so that the observer views the images superimposed as a composite image 59, as shown in FIG. 2c. As can be seen in the example, the treated area 55' in the matched portal image, overlays the tumor 51' in the matched simulation image. In another type of display (not shown), the outline of the treated area from the portal image is projected onto the processed simulation image, so that it can be seen if the targeted tumor was in fact treated.

In performing the coarse alignment, a coarse transformation is applied to the digitized x-ray or portal image signals (DPIS) to convert them to the coordinate system of the digital reference or simulation image signals (DSIS). As will be seen, the information needed to generate this transformation can be generated interactively through selection of what appear to be corresponding points in the two images by the operator interactively using a pointer device 43 or automatically using x-ray opaque fiducials 61 which are placed on the patient in both the simulation setup and the treatment setup (see FIG. 1). The points so generated in either case are referred to as seed points. The coarse transform H from the portal image coordinates to the simulation coordinates is:

$$\begin{bmatrix} simulation_x \\ simulation_y \\ 1 \end{bmatrix} = \begin{bmatrix} RotSkewScale_a & RotSkewScale_b & translation_x \\ RotSkewScale_c & RotSkewScale_d & translation_y \\ 0 & 0 & 1 \end{bmatrix} \cdot \begin{bmatrix} portal_x \\ portal_y \\ 1 \end{bmatrix}$$ (EQ. 1)

The (x y) vector denotes the column and row coordinates of the center of each of the seed points in the corresponding portal and simulation images. The four RotSkewScale components of the matrix describe the full affine transformation that is needed to coarsely align the images. In this stage, the placement of the fiducial or the interactive selection of the seed points need not be accurate as the next stage is able to accommodate for reasonably small deviations.

Using the results of the coarse alignment, the portal image is warped toward the simulation image. Then, overlapping regions of the two images are computer enhanced so that the corresponding intensity levels are similar. Finally, the motion-flow, or the fine-scale transform is computed so that the portal image glides on the gradient of dissimilarity toward the simulation image. In this stage, a more comprehensive transformation model is used in which the input position vector is represented by:

$$\underline{X}(x) = \begin{bmatrix} 1 & x & y & 0 & 0 & x^2 & x \cdot y & 0 \\ 0 & 0 & 0 & 1 & x & y & x \cdot y & y^2 & x^2 \end{bmatrix}$$ (EQ. 2)

and the transformation matrix is represented by:

$$Q = [\alpha_0 \alpha_1 \alpha_2 \alpha_3 \alpha_4 \alpha_5 P_0 P_1 c]^T$$ (EQ. 3)

so that the result is:

$$u(x;Q) = X(x) \cdot Q$$ (EQ. 4)

where $\Delta$ portal $(x;Q) = u(x;Q)$ and portal $(x) = X(x)$. The parameters $\alpha_0$ through $\alpha_5$ include the affine transform as in the coarse alignment, whereas the parameters $P_0$, $P_1$ include the perspective transformation, and c covers the deformation that can be caused by breathing, etc.

To recover the parameters of the vector Q we formulate the image dissimilarity as a result of motion-flow, or distance between the two images.

$$I(x,t) = I(x - (X(x) \cdot Q_{f,t+1}))$$ (EQ. 5)

for $\forall x \in f$, where $f$ is the region of the image we compute the transformation over. In (EQ. 5), I(x) is the intensity function at point x, the image at t+1 is the portal image, and at t is the simulation image. By using various derivation techniques, we formulate the motion-flow using the gradient (or dissimilarity gradient) as below:

$$\nabla I(\underline{X}(x) \cdot Q_f) + \frac{\partial I}{\partial t} = 0$$ (EQ. 6)

for $\forall x \in f$.

In this stage, a robust regression method is employed, using unconstrained optimization, to calculate the elements of Q (see (EQ. 3)). This technique enables us to cope with the 'reasonably small' deviations from the coarse alignment stage, as well as any residual dissimilarity between the two images. Using the robust technique ensures that only the dominant transformation will be recovered without running into the risk of being affected by the noise and residual errors.

Figure 3:
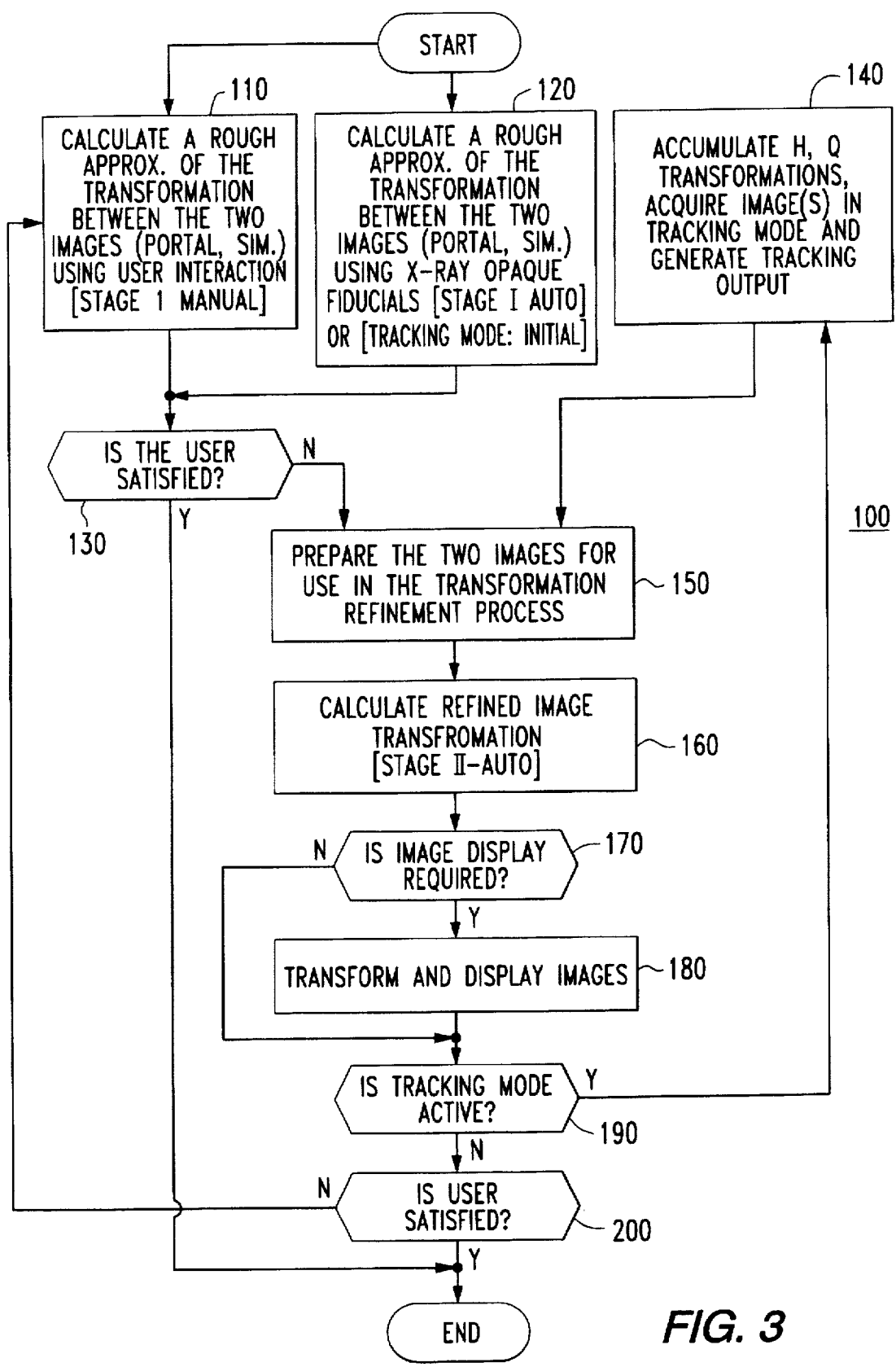
FIGS. 3–11 are flow charts of software utilized to implement the invention in the apparatus of FIG. 1.

FIGS. 3–11 are flow charts of software which implements the invention. FIG. 3 illustrates the main routine 100 which includes performing a coarse alignment, either interactively at block 110 or automatically at block 120. In both cases a rough approximation of the transformation between the portal image and the simulation image is calculated using Equation 1. The user then has the option of determining whether the rough approximation has provided a satisfactory alignment of the images at 130. If so, the procedure is completed. If not, a fine alignment is performed. As discussed, the invention can also be used to track patient movement, in which case the transformation between the two images is utilized at 140 to roughly determine the updated position of the fiducials. If requested by the user in image matching and during tracking, the images are prepared for the fine alignment at 150. The refined image transformation is then calculated at 160 and if the image matching mode is selected as determined at 170, the transform is accomplished and the images are displayed at 180 in the manner discussed above. If the tracking mode has been selected at 190, the routine returns to 140 for generating the next position. The user again has the final decision at 200 to determine whether the image matching is satisfactory. If not, the routine returns to 110 and the rough calculation is re-initiated.

Figure 4:
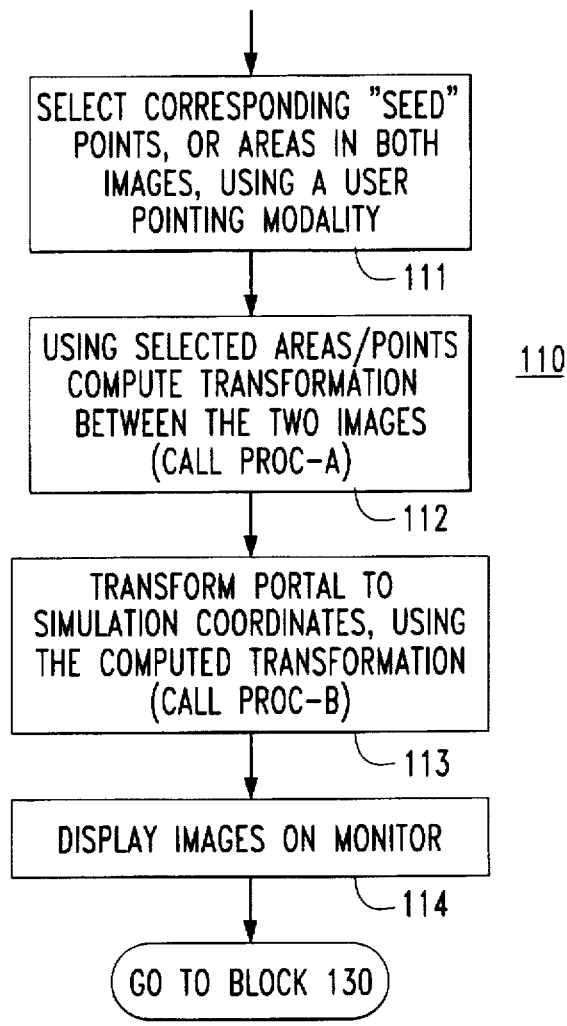

The procedure for calculating the rough approximation of the transformation interactively called for at block 110 in FIG. 3 is illustrated in detail in FIG. 4. The user selects corresponding seed points or areas in the portal image and the simulation image using, for instance, the mouse 43 as indicated at 111. The selected areas or points are then used to compute the rough transformation between the portal image and the simulation image by calling a procedure A as indicated at 112. This rough transform is then used to transform the portal image to simulation image coordinates by calling procedure B as indicated at 113. The images are then displayed on the monitor 37 as indicated at 114.

Figure 5:
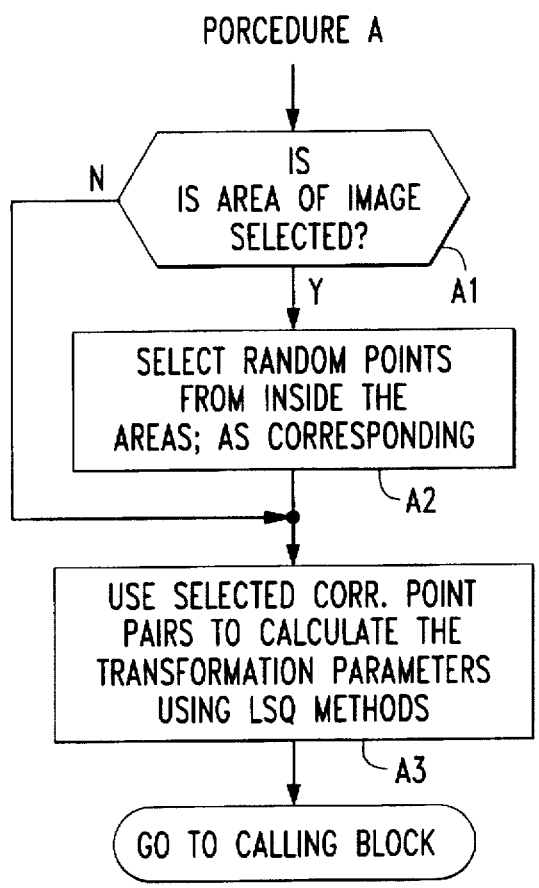

The details of procedure A used to calculate the rough transform are shown in FIG. 5. If the user has indicated an area as determined at A1, the system automatically selects random points from inside the area as corresponding as indicated at A2. Then, or if the user has selected points rather than an area, the corresponding point pairs are used to calculate the transform parameters using the least squares (LSQ) method as indicated at A3.

The details of procedure B for transforming the portal to simulation coordinates is shown in FIG. 5. First, the row and column limits of the resulting transformed portal image are determined at B1 using the transformation matrix H, which is the inverse of Equation 1. The resulting portal image is then raster scanned at B2, and for each pixel the location is determined using the transformation. The intensity value for each pixel is calculated next using linear interpolation between the surrounding pixel locations in the original portal image.

Figures 6, 8:
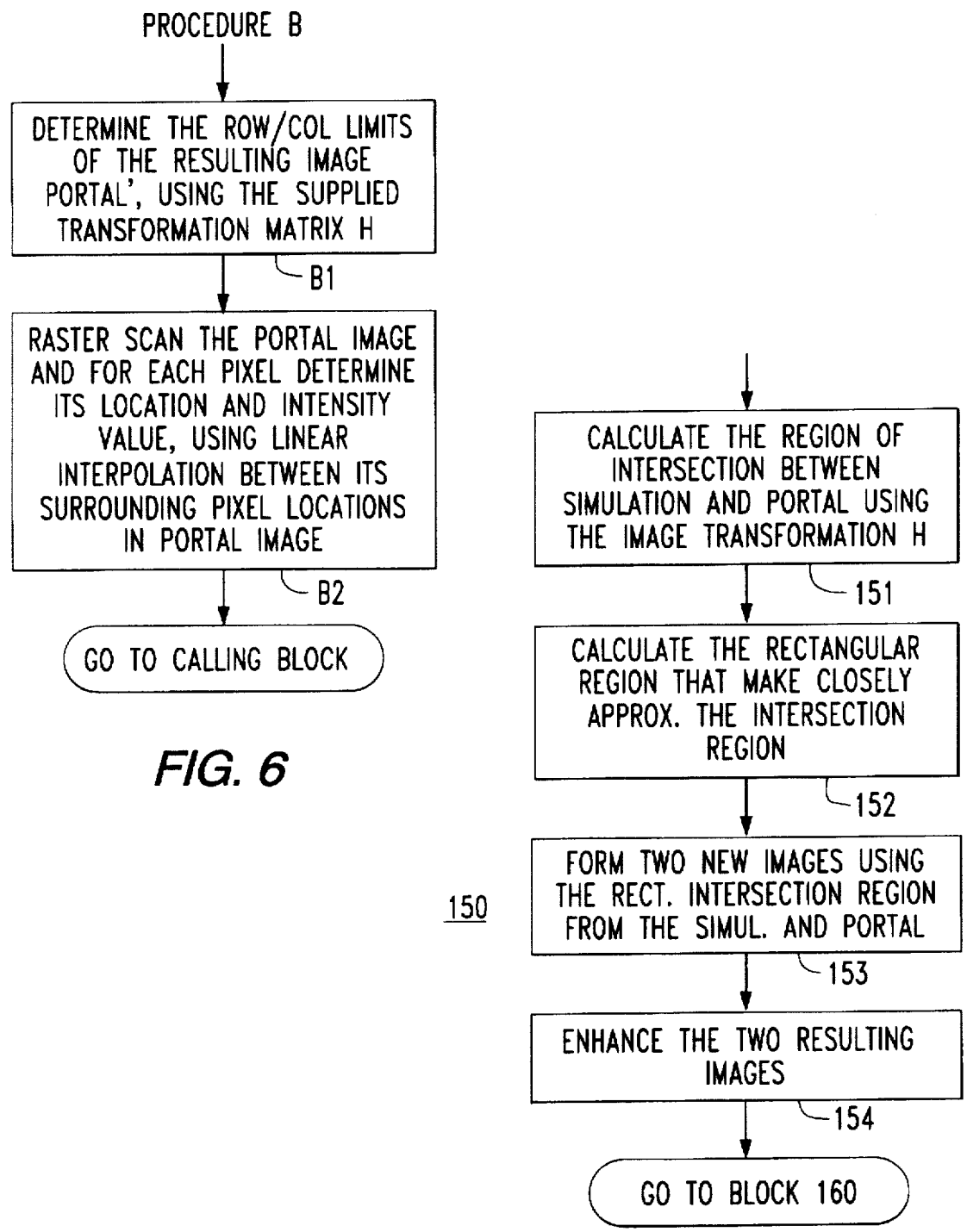
Figures 7, 11:
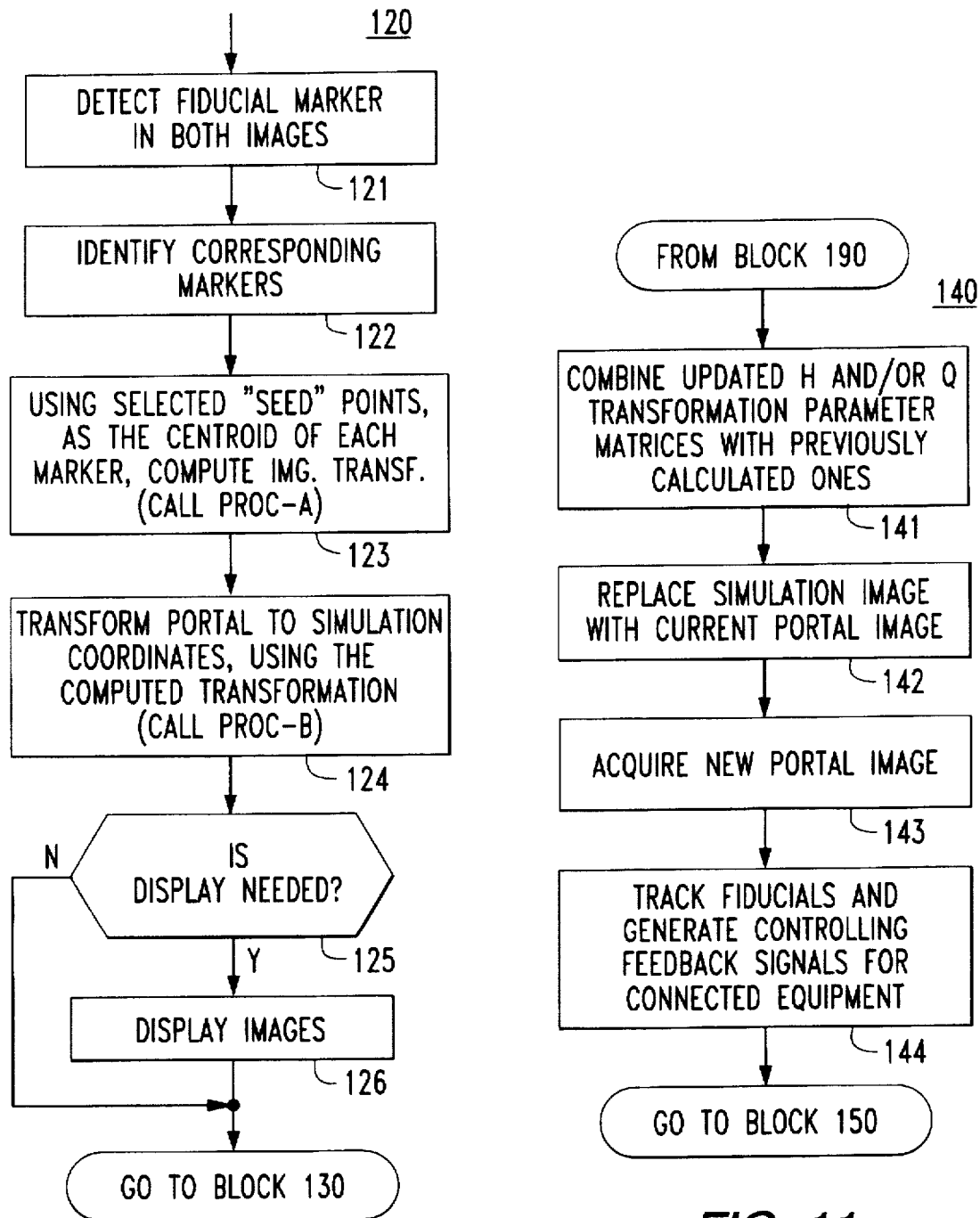

The routine 124 for performing the coarse alignment automatically using fiducials on the patient is shown in FIG. 7. The x-ray opaque fiducials 61 are detected in both the portal and simulation images at 121 and the corresponding markers are identified at 122. The image transform is then computed at 123 using procedure A of FIG. 5 and the centroid of each of the markers as the seed points. The portal image is then transformed to simulation coordinates using the computed transformation and procedure B of FIG. 6. When in the matching mode as determined at 125, the images are displayed at 126 in the manner discussed above in connection with FIGS. 2a–c.

The routine 150 for preparing the coarse aligned digital image signals for fine alignment is shown in FIG. 8. First, the region of intersection over overlap between the simulation and portal images is calculated at 151 using the transformation of Equation 1. Next, the largest rectangular region that fits within the intersection region is calculated at 152. Other regular geometric shapes, such as a square and so forth, could be used in place of the rectangle. New images representing the rectangular intersection region of the portal and simulation image are formed at 153. These resulting images are then enhanced at 154 to generate prepared digital image signals. Various forms of enhancement such as histogram equalization, lapalcian of the Gaussian, high-pass filtering and other techniques are used to produce the prepared images with similar dynamic range and pixel intensities.

Figure 9:
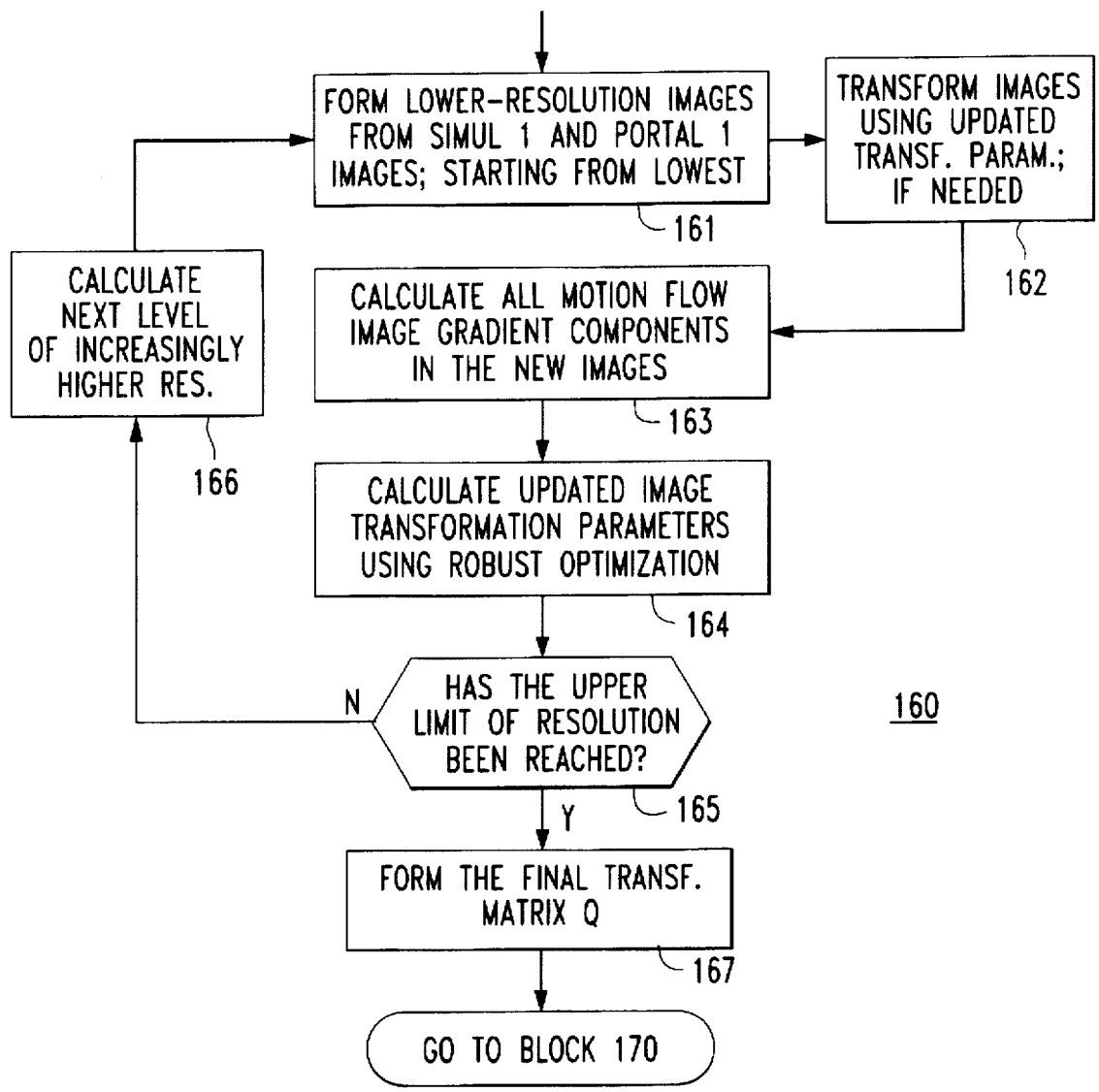

FIG. 9 illustrates the routine 160 for calculating the updated transformation for a fine alignment. This process is performed at several levels of resolution of the digital image signals beginning with the lowest resolution, which in the example is about one-eighth resolution. Thus, at 161 the images at the lowest resolution for the prepared portal and simulation images are formed. These images are updated using the latest updated transformation parameters, that is, transformation parameters calculated at the previous level of resolution, at 162. An important part of the invention is that robust motion flow is used to perform the fine alignment. In particular, the motion flow gradient components are generated at 163. Application of motion flow using gradient components is described by M. J. Black and P. Anandan in a paper entitled, "*A Framework For The Robust Estimation Of Optical Flow*" published in Proc. 4th Intl. Conf. on Computer Vision (ICCV 93), Berlin, Germany, May 1993. Motion flow is applied to the motion required to cause pixels on one image to flow into alignment with corresponding pixels in the other image. Robust motion applies to the motion by which most of the pixels which have moved have moved similarly, while there may be others exhibiting different motion. The updated image transformation parameters are then calculated at 164 using robust optimization. If the upper limit of resolution has not been reached as determined at 165, then the resolution is incremented at 166 and updated transformation parameters are recalculated at the new level of resolution.

Figure 10:
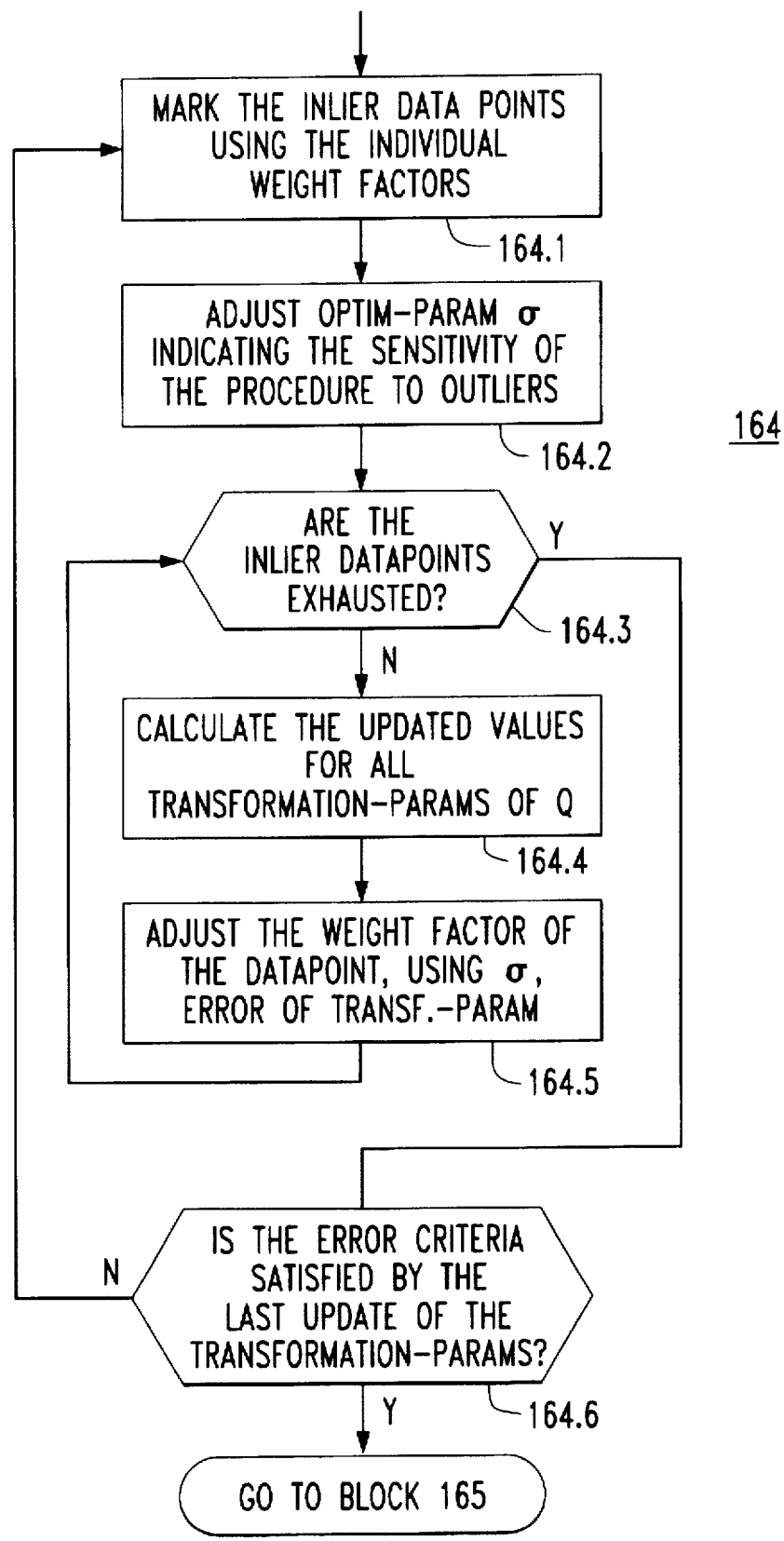

When the highest level of resolution has been reached at 165, the final transformation matrix Q is generated at 167. The details of the routine for calculating the updated image transformation parameters using robust optimization of block 164 in FIG. 9 is shown in FIG. 10. As described in the paper by Black and Anandan discussed above, the robust motion is represented by data points called inliers. Those exhibiting other motion are identified as outliers. In the present invention, the data points are the pixel values. The pixels are successively separated into inliers and outliers based upon their contribution to a consistent motion flow vector. The pixels in the inlier set are used to calculate the dominant motion flow, and their contribution to it is dependent on their weight factors which are calculated during the robust optimization.

Referring particularly to FIG. 10, a loop is entered at 164.1 where each of the inlier points is marked using individual weight factors. Initially, the weight factors of the pixels are all set to 1 so that all of the pixels are inliers. At 164.2, an optimization parameter, $\sigma$, which determines the sensitivity of the procedure to outliers is set. The weight factors are dependent on this parameter, $\sigma$. The lower the value of $\sigma$, the more points are eliminated as inliers and the closer the inliers become to the current estimate of the motion flow vector. Hence, a large $\sigma$ is used initially so that all points are included. On successive loops, $\sigma$ is lowered to eliminate more and more outliers. This lowering of $\sigma$ is referred to as $\sigma$ scheduling. The $\sigma$ scheduling must be done carefully. If $\sigma$ is lowered too fast, a solution may be missed, while on the other hand, lowering $\sigma$ too slowly increases the processing time. In accordance with the invention, $\sigma$ is lowered depending upon the largest error in the motion flow parameters. Following this, another loop is entered at 164.3 in which each of the inlier data points is used in the calculation of the updated values for the transformation parameters of the Q matrix at 164.4. The equations used at 164.4 are derived preferably using the conjugate gradient, although gradient descent can also be used. In addition, motion flow and robust statistics are used in deriving equations for determining the transformation parameters. The error in the transformation parameters, which is the change from the last calculation, as well as σ, are used at 164.5 to adjust the weight factors for the pixels. When all of the inlier data points/pixels have been used as determined at 164.3, a check is made at 164.6 to determine if the solution has converged to the desired degree. If not, the routine returns to 164.1 and the inlier data points are again marked using the updated weight factors.

FIG. 11 illustrates the tracking routine on 140. As indicated at 141, the incremental updates and the transform H and/or Q are combined so that the transform always relates back to the original simulation or reference image. On the initial pass through the tracking routine, the then current portal image replaces the simulation image if used, and then a new portal image is acquired at 143. As tracking continues, successive portal images are matched with the next preceding portal image to generate the updated transform. As indicated at 144, the successive positions of the fiducials or changes in the pattern of the fiducials from successive portal images is used to generate tracking signals for controlling the radiotherapy equipment such as turning the beam on and off and/or driving the patient positioning assembly.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. Apparatus for automatically matching a portal image with a simulation image, said apparatus comprising:

means digitizing said portal image and simulation image to generate digital portal image signals (DPIS) and digital simulation image signals (DSIS), respectively;

processing means processing said DPIS and said DSIS to generate matched DPIS and DSIS; and output means for generating an output from said matched DPIS and DSIS.

2. The apparatus of claim 1, wherein said processing means comprises coarse alignment means generating coarse aligned DPIS and DSIS from said DPIS and DSIS, and fine alignment means generating said matched DPIS and DSIS from said coarse aligned DPIS and DSIS for overlapping regions of said simulation and portal images.

3. The apparatus of claim 2, wherein said coarse alignment means comprises means selecting corresponding seed points in said portal image represented by said DPIS and said simulation image represented by said DSIS, means computing a transform between said portal image and said simulation image from said corresponding seed points, and means applying said transform to one of said DPIS said DSIS to generate with the other of said DPIS and DSIS said coarse aligned DPIS and DSIS.

4. The apparatus of claim 3, wherein said means selecting corresponding seed points comprises interactive means selecting corresponding points in displays generated from said DPIS and DSIS.

5. The apparatus of claim 3, wherein said means selecting corresponding seed points comprises means detecting x-ray opaque fiducials in said DPIS and said DSIS, and means identifying corresponding fiducials in said DPIS and DSIS as said corresponding seed points.

6. The apparatus of claim 3, wherein said fine alignment means comprises means generating prepared DPIS and DSIS from said coarse aligned DPIS and DSIS, means generating an updated transform from said prepared DPIS and DSIS, and means applying said updated transform to one of said coarse and prepared DPIS and DSIS to generate said matched DPIS and DSIS.

7. The apparatus of claim 2, wherein said fine alignment means comprises means generating prepared DPIS and DSIS from said coarse aligned DPIS and DSIS, means generating an updated transform from said prepared DPIS and DSIS, and means applying said updated transform to one of said coarse and prepared DPIS and DSIS to generate said matched DPIS and DSIS.

8. The apparatus of claim 7, wherein said means generating said prepared DPIS and DSIS comprises means selecting selected DPIS and selected DSIS for regions of images represented by said DPIS and DSIS which intersect.

9. The apparatus of claim 8, wherein said means generating said prepared DPIS and DSIS further includes means enhancing said selected DPIS and DSIS.

10. The apparatus of claim 9, wherein said means selecting said selected DPIS and selected DSIS further includes means selecting DPIS and DSIS within a portion of regions of images represented by said DPIS and DSIS, which have a predetermined regular shape.

11. The apparatus of claim 7, wherein said means generating said updated transform comprises means generating motion flow components from said prepared DPIS and DSIS and calculating means calculating said updated transform from said motion flow components.

12. The apparatus of claim 11, wherein said means generating motion flow components generates motion flow gradient components, and said calculating means comprises means applying a robust optimization to calculate said updated transform.

13. The apparatus of claim 12, wherein said means generating said updated transform comprises utilizing said means generating motion flow gradient components and said calculating means repetitively using successive ascending levels of resolution of said prepared DPIS and DSIS.

14. The apparatus of claim 7, wherein said means generating said updated transform comprises means using successive ascending levels of resolution of said prepared DPIS and DSIS to generate said updated transform.

15. The apparatus of claim 7, wherein said means generating said updated transform comprises means applying robust motion flow to said prepared DPIS and DSIS.

16. The apparatus of claim 15, wherein said means applying robust motion flow to said prepared DPIS and DSIS applies robust motion flow to successive ascending levels of resolution of said DPIS and DSIS.

17. The apparatus of claim 1, wherein said output means comprises display means generating a display from said matched DPIS and DSIS.

18. The apparatus of claim 1, wherein said output means comprises tracking means tracking movement in said image represented by said DPIS.

19. The apparatus of claim 18, wherein said output means further includes positioning means positioning a patient relative to a radiation beam which generates said portal image, and means controlling said positioning means in response to movement tracked by said tracking means.

20. The apparatus of claim 18 wherein said output means includes means controlling generation of a radiation beam producing said portal image in response to movement tracked by said tracking means.

21. Apparatus for matching portal images to control radiotherapy/diagnosis equipment, said apparatus comprising:

means digitizing successive portal images to generate successive sets of digital portal image signals (DPIS); and tracking means tracking movement between successive sets of DPIS.

22. The apparatus of claim 21, wherein said tracking means comprises means generating an updated transform between successive portal images by applying robust motion flow to said successive sets of DPIS and means using said updated transform to track said movement between said successive sets of DPIS.

23. The apparatus of claim 22, wherein said means generating said updated transform comprises means generating motion flow components from said successive sets of DPIS, and means calculating said updated transform between successive portal images using said motion flow components.

24. The apparatus of claim 23, wherein said means generating motion flow components generates motion flow gradient components, and wherein said calculating means comprises means applying a robust optimization to calculate said updated transform.

25. The apparatus of claim 24, wherein said means generating said updated transform comprises means utilizing said means generating motion flow gradient components and said calculating means repetitively using successive ascending levels of resolution of said successive sets of DPIS.

26. Apparatus for automatically matching an x-ray image with a reference image, said apparatus comprising:

means digitizing said x-ray image and reference image to generate first digital image signals and second digital image signals, respectively;

processing means processing said first and second digital signals without input of any physical dimensions of any features within said images to generate matched digital image signals; and display means generating a display from said matched digital image signals.

27. The apparatus of claim 26 wherein said processing means comprises coarse alignment means generating coarse aligned digital images signals from said first and second digital image signals, and fine alignment means generating a transform between said coarse aligned digital image signals for overlapping regions of said x-ray and reference images utilizing robust motion flow, and means applying said transform to one of said coarse aligned digital image signals to generate said matched digital image signals.

28. The apparatus of claim 27 wherein said fine alignment means comprises means enhancing said coarse aligned digital image signals to generate prepared coarse aligned image signals having similar dynamic ranges and intensities, and means generating said transform between said prepared coarse aligned digital image signals utilizing robust motion flow.

* * * * *

UNITED STATES PATENT AND TRADEMARK OFFICE
CERTIFICATE OF CORRRECTION

Page 1 of 2

PATENT NO. : 5,784,431
DATED : July 21, 1998
INVENTOR(S) : Kalend, et al.

It is certified that error appears in the above-identified patent and that said Letters Patent is hereby corrected as shown below:

At [56] References Cited, please add the following patents and publications.

OTHER DOCUMENTS

| | | |
|---|---|---|
| | | Digital portal image registration by sequential anatomical matchpoint and image correlations for real-time continuous field alignment verification, Brian J. McParland and J. Carl Kumaradas, Phys. 22(7), July 1995, pp. 1063-1075. |
| | | Neutral Network Object Recognition for Inspection of Patient Setup in Radiation Therapy Using Portal Images, Susan S. Young, et al., 1996 IEEE, pp. 3418-3421. |

UNITED STATES PATENT AND TRADEMARK OFFICE
CERTIFICATE OF CORRECTION

PATENT NO. : 5,784,431
DATED : July 21, 1998
INVENTOR(S) : Kalend, et al.

It is certified that error appears in the above-identified patent and that said Letters Patent is hereby corrected as shown below:

Column 9, line 37, after "means" insert --comprising coarse alignment means--.

Column 9, line 38, after "generate" insert --coarse aligned DPIS and DSIS, means determining from said coarse aligned DPIS and DSIS overlapping regions of said simulation and portal images, and fine alignment means generating--.

Column 9, line38, after "DSIS" insert --from said coarse aligned DPIS and DSIS for said overlapping regions of said simulation and portal images--.

Cancel Claim 2.

Column 9, line 47, change "2" to --1--.

Column 10, line 5, change "2" to --1--.

Signed and Sealed this

Twenty-third Day of February, 1999

Attest:

Q. TODD DICKINSON

*Attesting Officer*    *Acting Commissioner of Patents and Trademarks*

(12) EX PARTE REEXAMINATION CERTIFICATE (8494th)
United States Patent
Kalend et al.

(10) Number: US 5,784,431 C1
(45) Certificate Issued: Aug. 30, 2011

(54) APPARATUS FOR MATCHING X-RAY IMAGES WITH REFERENCE IMAGES

(75) Inventors: Andre M. Kalend, Monroeville, PA (US); Joel Greenberger, Sewickley, PA (US); Karun B. Shimoga, Pittsburgh, PA (US); Charalambos N. Athanassiou, Athens (GR); Takeo Kanade, Pittsburgh, PA (US)

(73) Assignee: University of Pittsburgh of the Commonwealth System of Education, Pittsburgh, PA (US)

Reexamination Request:
No. 90/009,531, Aug. 6, 2009

Reexamination Certificate for:
Patent No.: 5,784,431
Issued: Jul. 21, 1998
Appl. No.: 08/739,622
Filed: Oct. 29, 1996

Certificate of Correction issued Feb. 23, 1999.

(51) Int. Cl.
*A61N 5/10* (2006.01)

(52) U.S. Cl. .............................. 378/65; 378/69; 378/901
(58) Field of Classification Search .................. None
See application file for complete search history.

(56) References Cited

U.S. PATENT DOCUMENTS

| | | | |
|---|---|---|---|
| 3,911,899 A | 10/1975 | Hattes | 128/2 S |
| 4,262,306 A | 4/1981 | Renner | 358/93 |
| 4,387,722 A | 6/1983 | Kearns | 128/716 |
| 4,459,990 A | 7/1984 | Barnea | 128/656 |
| 4,679,076 A | 7/1987 | Vikterlof et al. | 358/107 |
| 4,706,296 A | 11/1987 | Pedotti et al. | 382/42 |
| 4,727,565 A | 2/1988 | Ericson | 378/205 |
| 4,969,200 A | 11/1990 | Manns et al. | 382/8 |
| 4,994,965 A | 2/1991 | Crawford et al. | 364/413.15 |
| 5,067,494 A | 11/1991 | Rienmueller et al. | 128/653.1 |
| 5,080,100 A | 1/1992 | Trotel | 128/653.1 |
| 5,207,223 A | 5/1993 | Adler | 128/653.1 |
| 5,254,948 A | 10/1993 | Sano et al. | 324/309 |
| 5,271,055 A | 12/1993 | Hsieh et al. | 378/95 |
| 5,278,915 A | 1/1994 | Chupeau et al. | 382/1 |
| 5,295,200 A | 3/1994 | Boyer | 382/43 |
| 5,295,483 A | 3/1994 | Nowacki et al. | 128/660.03 |
| 5,389,101 A | 2/1995 | Heilbrun et al. | 606/130 |
| 5,434,903 A | 7/1995 | Hoornaert et al. | 378/116 |
| 5,446,548 A | 8/1995 | Gerig et al. | 356/375 |
| 5,447,154 A | 9/1995 | Cinquin et al. | 128/653.1 |

(Continued)

FOREIGN PATENT DOCUMENTS

| | | |
|---|---|---|
| EP | 0 153 439 B1 | 9/1985 |
| FI | 861600 | 9/1989 |
| JP | 8-126638 | 5/1996 |

OTHER PUBLICATIONS

R. Bajcsy and S. Kovacic, Multiresolution Elastic Matching, Computer Vision, Graphics, and Image Processing 46, 1–21 (1989).*

(Continued)

*Primary Examiner* — Margaret Rubin

(57) ABSTRACT

X-ray images such as radiotherapy portal images and simulation images are matched by apparatus which digitizes the images and automatically processes the digitized signals to generate matched digitized signals which can be displayed for comparison. The digitized images are first coarse aligned using a transform generated from seed points selected interactively from the two images or through detection and identification of x-ray opaque fiducials placed on the patient. A fine alignment is then performed by first selecting intersecting regions of the two images and enhancing those regions. Secondly, an updated transform is generated using robust motion flow in these regions at successive ascending levels of resolution. The updated transform is then used to align the images which are displayed for comparison. The updated transform can also be used to control the radiotherapy equipment.

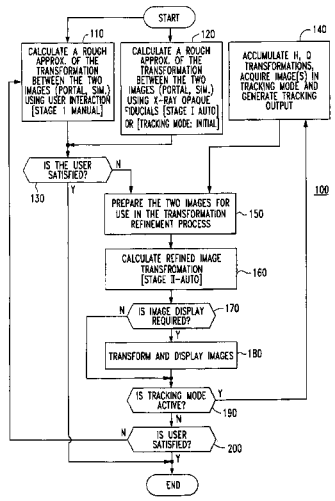

U.S. PATENT DOCUMENTS

| | | | |
|---|---|---|---|
| 5,482,042 A | 1/1996 | Fujita | 128/653.1 |
| 5,485,833 A | 1/1996 | Dietz | 128/204.23 |
| 5,538,494 A | 7/1996 | Matsuda | 600/1 |
| 5,588,430 A | 12/1996 | Bova et al. | 128/653.1 |
| 5,622,187 A | 4/1997 | Carol | 128/897 |
| 5,673,300 A | 9/1997 | Reckwerdt et al. | 375/65 |
| 5,740,225 A | 4/1998 | Nabatame | 378/65 |
| 5,758,645 A | 6/1998 | Qian | 128/653.1 |
| 5,820,553 A | 10/1998 | Hughes | 600/426 |
| 5,967,980 A | 10/1999 | Ferre et al. | 600/424 |

OTHER PUBLICATIONS

T. Radcliffe, R. Rajapakshe, and S. Shalev, Pseudocorrelation: A Fast, Robust, Absolute, Grey–Level Image Alignment Algorithm, Med. Phys., vol. 21, issue 6 (published Jun. 1994) ("Radcliffe").

Michael J. Black and P. Anandan, A Framework for the Robust Estimation of Optical Flow, Proc. Fourth Int. Conf. on Computer Vision, ICCV 93, Berlin, Germany (published May 1993) ("Black").

K.G.A. Gilhuijs and M. van Herk, Automatic On–Line Inspection of Patient Setup in Radiation Therapy Using Digital Portal Images, Med. Phys., vol. 20, issue 6 (published May/Jun. 1993) ("Gilhuijs").

J. Bijhold, K.G.A. Gilhuijs, and M. van Herk, Automatic Verification of Radiation Field Shape Using Digital Portal Images, Med. Phys., vol. 19, issue 4 (published Jul./Aug. 1992) ("Bijhold").

K. Eilertsen, A. Skretting, and T.L. Tennvassas, Method For Fully Automated Verification of Patent Set–up In External Beam Radiotherapy With Polygon Shaped Fields, Phys. Med. Bio. vol. 39 (published 1994) ("Eilertsen").

Ahlstrom et al., "Pulmonary MR Angiography with Ultrasmall Superparamagnetic Iron Oxide Particles as a Blood Pool Agent and a Navigator Echo for Respiratory Gating: Pilot Study," Radiology, vol. 211, No. 3, pp. 865–869, Jun. 1999.

Anandan, "A Computational Framework and an Algorithm for the Measurement of Visual Motion," International Journal of Computer Vision, 2, pp. 283–310, 1989.

Antonuk et a., "A High–Resolution, High Frame Rate, Flat–Panel TFT Array for Digital X–Ray Imaging," Proceedings of SPIE, vol. 2163. pp. 118–128, 1994.

Axel et al., "Respiratory Effect in Two–Dimensional Fourier Transform MR Imaging," Radiology, vol. 160, No. 3, pp. 795–801, Sep. 1986.

Baily et al., "Fluroscopic Visualization of Megavoltage Therapeutic X Ray Beams," Int. J. Radiation Oncology Biol. Phys., vol. 6, pp. 935–939, 1980.

Ballard et al., "Computer Vision," Prentice Hall, pp. 65–72, 102–113, and 199–207, 1982.

Balter et al., "Correlation of Projection Radiographs in Radiation Therapy Using Open Curve Segments and Points," Am. Assoc. Phys. Med. 19 (2), pp. 329–334, 1992.

Balter et al., "Uncertainties in CT–Based Radiation Therapy Treatment Planning Associated with Patient Breathing," Int. J. Radiation Oncology Biol. Phys., vol. 36, No. 1, pp. 167–174, 1996.

Baroni et al., "Optoelectronic Techniques for Patient Repositioning in Radiotherapy," Technology and Health Care, vol. 4, Issue 3, pp. 251–565, accepted Nov. 15, 1995.

Baroni et al., "Real–Time Motion Analysis for Definition and Control of Patient Position in Radiotherapy," SPIE vol. 2709, pp. 506–515, 1996.

Behbehani et al., "A Microprocessor–Based Sleep Apnea Ventilator," IEEE Engineering in Medicine and Biology, 11th Annual International Conference, pp. 332–333, 1989.

Bel et al., "A Verification Procedure to Improve Patient Set–Up Accuracy Using Portal Images," Radiotherapy and Oncology 29, pp. 253–260, 1993.

Bijhold et al., "Fast Evaluation of Patient Set–Up During Radiotherapy by Aligning Features in Portal and Simulator Images," Phys. Med. Biol., vol. 36, No. 12, pp. 1665–1679, 1991.

Bijhold et al., "Radiation Field Edge Detection in Portal Images," Phys. Med. Biol., vol. 36, No. 12, pp. 1705–1710, 1991.

Bijhold, J., "Three–Dimensional Verification of Patient Placement During Radiotherapy Using Portal Images," Am. Assoc. Phys. Med. 20 (2), pp. 347–356, 1993.

Bissett et al., "Quantitative VS. Subjective Portal Verification Using Digital Portal Images," Int. J. Radiation Oncology Biol. Phys., vol. 34, No. 2, pp. 489–495, 1996.

Bissett et al., "Radiotherapy Portal Verification: An Observer Study," The British Journal of Radiology, 68, pp. 165–174, 1995.

Bohning et al., "PC–Based System for Retrospective Cardiac and Respiratory Gating of NMR Data," Magnetic Resonance in Medicine, vol. 16, pp. 303–316, 1990.

Boyer et al., "A Portal Image Correlation Procedure," Medical Physics, vol. 19, No. 3, p. 802, May/Jun. 1992 (Abstract).

Boyer, A., "Present and Future Developments in Radiotherapy Treatment Units," Seminars in Radiation Oncology, vol. 5, No. 2, pp. 146–155, Apr. 1995.

Cootes et al., "Active Shape Models—Smart Snakes," In Proc. BMVC, pp. 266–275, Leeds, UK, 1992.

Cootes et al., "Training Models of Shape from Sets of Examples," In Proc. BMVC, pp. 9–18, Leeds, UK, 1992.

Crooks et al., "Contrast Enhancement of Portal Images by Selective Histogram Equalization," Am. Assoc. Phys. Med. 20 (1), pp. 199–204, 1993.

Davatzikos et al., "Image Registration Based on Boundary Mapping," IEEE Transactions on Medical Imaging, vol. 15, No. 1, pp. 112–115, Feb. 1996.

Debois et al., "Verification of Lung Position and Inflation for Breath Hold Treatment of Lung Tumors Using On–Line Imaging," Med. Phys. vol. 23, No. 6, pp. 1082–1083, Jun. 1996.

De Neve et al., "Interactive Use of On–Line Portal Imaging in Pelvic Radiation," Int. J. Radiation Oncology Biol. Phys., vol. 25, pp. 517–524, 1993.

De Neve et al., "Routine Clinical On–Line Portal Imaging Followed by Immediate Field Adjustment Using a Tele–Controlled Patient Couch," Radiotherapy and Oncology, 24, pp. 45–54, 1992.

Dong et al., "An Image Correlation Procedure for Digitally Reconstructed Radiographs and Electronic Portal Images," Int. J. Radiation Oncology Biol. Phys., vol. 33, No. 5, pp. 1053–1060, 1995.

Dong et al., An Objective Method for Evaluating Electronic Portal Imaging Devices, Am. Assoc. Phys. Med. 21 (6), pp. 755–760, 1994.

Ehman et al., "Magnetic Resonance Imaging with Respiratory Gating: Techniques and Advantages," AJR, vol. 43, pp. 1175–1182, Dec. 1984.

Essers et al., "Transmission Dosimetry with a Liquid–Filled Electronic Portal Imaging Device," Int. J. Radiation Oncology Biol. Phys., vol. 34, No. 4, pp. 931–941, 1996.

Evans et al., "Image Comparison Techniques for Use with Megavoltage Imaging Systems," The British Journal of Radiology, 65, pp. 701–709, 1992.

Ferrigno et al., "Three–Dimensional Optical Analysis of Chest Wall Motion," J. Appl. Physiology, vol. 77, Issue 3, pp. 1224–1231, 1994.

Fritsch et al., "Core–Based Portal Image Registration for Automatic Radiotherapy Treatment Verification," Int. J. Radiation Oncology Biol. Phys., vol. 33, No. 5, pp. 1287–1300, 1995.

Fritsch et al., "Cores for Image Registration," Proc. SPIE Med. Imaging '94, Image Processing, pp. 1–15, 1994.

Gall et al., "A System for Diagnostic Quality Radiographic Alignment of Radiotherapy Patients," Int. J. Radiation Oncology • Biology • Physics, vol. 36, No. 1, Supplement, p. 206, 1996.

Gerig et al., "The Development and Clinical Application of a Patient Position Monitoring System," Int. J. Radiation Oncology Biol. Phys., vol. 27, Supp. 1, p. 163, 1993.

Gerig et al., "The Development and Clinical Application of a Patient Position Monitoring System," Proc. of SPIE, Videometrics III, vol. 2350, pp. 59–72, Oct. 6, 1994.

Gildersleve et al., "A Randomised Trial of Patient Repositioning During Radiotherapy Using a Megavoltage Imaging System," Radiotherapy and Oncology 31, pp. 161–168, 1994.

Gildersleve et al., "Reproducibility of Patient Positioning During Routine Radiotherapy, as Assessed by an Integrated Megavoltage Imaging System," Radiotherapy and Oncology 35, pp. 151–160, 1995.

Gilhuijs et al., "An Algorithm for Automatic Analysis of Portal Images: Clinical Evaluation for Prostate Treatments," Radiotherapy and Oncology 29, pp. 261–266, 1993.

Gilhuijs et al., "Automatic On–Line Patient Setup Analysis in Portal Images," 6th International Conference Image Analysis and Processing (Como, Italy), pp. 629–636, 1991.

Gilhuijs et al., "Automatic Three–Dimensional Inspection of Patient Setup in Radiation Therapy Using Portal Images, Simulator Images, and Computed Tomography Data," Med. Phys. 23 (3), pp. 389–399, Mar. 1996.

Gilhuijs et al., "Interactive Three Dimensional Inspection of Patient Setup in Radiation Therapy Using Digital Portal Images and Computed Tomography Data," Int. J. Radiation Oncology Biol. Phys., vol. 34, No. 4, pp. 873–885, 1996.

Gilhuijs et al., "Optimization of Automatic Portal Image Analysis," Am. Assoc. Phys. Med 22 (7), pp. 1089–1099, Jul. 1995.

Graham et al., A Method to Analyze 2–Dimensional Daily Radiotherapy Portal Images from An On–Line Fiber–Optic Imaging System, Int. J. Radiation Oncology Biol. Phys., vol. 20, pp. 513–619, 1991.

Graham et al., "Preliminary Results of a Prospective Trial Using Three Dimensional Radiotherapy for Lung Cancer," Int. J. Radiation Oncology Biol. Phys., vol. 33, No. 5, pp. 993–1000, 1995.

Halverson et al., "Study of Treatment Variation in the Radiotherapy of Head and Neck Tumors Using a Fiber Optic On–Line Radiotherapy Imaging System," Int. J. Radiation Oncology Biol. Phys., vol. 21, pp. 1327–1336, 1991.

Hartford et al., "Conformal Irradiation of the Prostate: Estimating Long–Term Rectal Bleeding Risk Using Dose–Volume Histograms," Int. J. Radiation Oncology Biol. Phys., vol. 36, No. 3, pp. 721–730, 1996.

Herman et al., "Clinical Use of On–Line Portal Imaging for Daily Patient Treatment Verification," Int. J. Radiation Oncology Biol. Phys., vol. 28, No. 4, pp. 1017–1023, 1994.

Hill et al., "Accurate Frameless Registration of MR and Ct Images of the Head: Application in Planning Surgery and Radiation Therapy," Radiology, vol. 191, No. 2, pp. 447–454, May 1994.

Humm et al., "Collison Detection and Avoidance During Treatment Planning," Int. J. Radiation Biol. Phys. vol. 33, No. 5, pp. 1101–1108, 1995.

Johnson et al., "Initial Clinical Experience with an Interactive, Video Based Patient–Positioning System for Head and Neck Treatment," Int. J. Radiation Oncology Biol. Phys., vol. 36, No. 1, Supplement, p. 204, 1996.

Jones et al., "Investigation of an FFT–Based Correlation Technique for Verification of Radiation Treatment Setup," Am. Assoc. Phys. Med. 18 (6) pp. 1118–1125, Nov./Dec. 1991.

Kalend et al., "An Artificial Computer Vision (AV) System Responsive to Patient Motions with Feedback for Computer Controlled Radiation Therapy," 6 pages.

Kessler et al., "A Graphical Simulator for Design and Verification of Computer–Controlled Treatment Delivery," Proceedings of the XIth International Conference on the use of Computers in Radiation Therapy, pp. 80–81, 1994.

Kessler et al., "Integration of Multimodality Imaging Data for Radiotherapy Treatment Planning," Int. J. Radiation Oncology Biol. Phys., vol. 21, pp. 1653–1667, 1991.

Kikinis, R., "3–D Imaging: Enhanced Reality," Medical Physics, vol. 23, No. 6, Jun. 1996.

Kim et al., "Effects of Spontaneous Respiration on Right and Left Ventricular Function: Evaluation by Respiratory and ECG Gated Radionuclide Ventriculography," J. Nucl. Med., vol. 38, pp. 173–177, 1987.

King et al., "High–Dose, Hyperfractinated, Accelerated Radiotherapy Using A Concurrent Boost for the Treatment of Nonsmall Cell Lung Cancer, Unusual Toxicity and Promising Early Results," Int. J. Radiation Oncology Biol. Phys., vol. 36, No. 3, pp. 593–599, 1996.

Komaki et al., "Apoptosis and Mitosis as Prognostic Factors in Pathologically Staged N1 Nonsmall Cell Lung Cancer," Int. J. Radiation Oncology Biol, Phys., vol. 36, No. 3, pp. 601–605, 1996.

Kubo, D., "Are Respiration Gated Treatment Feasible?" Medical Physics, vol. 23, No. 6, p. 1148, Jun. 1996.

Kubo et al., "Respiration Gated Radiotherapy Treatment: A Technical Study," Phys. Med. Biol. 41, pp. 83–91, 1996.

Kupelian et al., "Prognostic Factors in the Treatment of Node–Negative Nonsmall Cell Lung Carcinoma with Radiotherapy Alone," Int. J. Radiation Oncology Biol. Phys., vol. 36, No. 3, pp. 607–613, 1996.

Lam et al., "On–Line Portal Imaging: Computer–Assisted Error Measurement," Radiology, vol. 179, No. 3, pp. 781–873, Jun. 1991.

Lebesque et al., "Detection of Systematic Patient Setup Errors by Portal Film Analysis," Radiotherapy and Oncology, 23, p. 196, 1992.

Leszczynski et al., "A Comparative Study of Methods for the Registration of Pairs of Radiation Fields," Phys. Med Biol., 38, pp. 1493–1502, 1993.

Leszczynski et al., "A Polygon Matching Algorithm and Its Applications to Verification of Radiation Field Placement in Radiotherapy," International Journal of Bio–Medical Computing 40, pp. 59–67, 1995.

Leszczynski et al., "A Study on the Efficacy of Digital Enhancement of On–Line Portal Images," Am. Assoc. Phys. Med. 19 (4), pp. 999–1005, Jul./Aug. 1992.

Leszczynski et al., "The Application of Three Registration Techniques to Clinical On–Line Portal Images," 7 pages.

Leszczynski et al., "Verification of Radiotherapy Treatments: Computerized Analysis of the Size and Shape of Radiation Fields," Am. Assoc. Phys. Med. 20 (3), pp. 687–694, May/Jun. 1993.

Lewis et al., "Comparison of Respiratory Triggering and Gating Techniques for the Removal of Respiratory Artifacts in MR Imaging," vol. 160, pp. 803–810, 1986.

Li et al., "Coronary Arteries: Three–Dimensional MR Imaging with Retrospective Respiratory Gating," Radiology, vol. 201, No. 3, Dec. 1996.

Lichter et al., "Recent Advances in Radiation Oncology," New England Journal of Medicine, vol. 332, No. 6, pp. 371–379, Feb. 9, 1995.

Lipcamon et al., "MRI of the Upper Abdomen Using Motion Artifact Suppression Technique (MAST)," Radiologic Technology, Vo. 59, No. 5, pp. 415–418, May/Jun. 1988.

Lopez et al., "An Artificial Neural Network Based Snore Detector," Annual International Conference of the IEEE Engineering in Medicine and Biology—Proceedings, vol. 16, p. 1107–1108, 1994.

Matthews et al., "Real–Time 3D Dose Calculation and Display: A Tool for Plan Optimization," Int. J. Radiation Oncology Biol. Phys., vol. 36, No. 1, pp. 159–165, 1996.

McKibben et al., "A Piezoelectric Respiratory Monitor for in Vivo NMR," Magnetic Resonance in Medicine, vol. 37, pp. 338–342, 1992.

McParland, B., "Uncertainty Analysis of Field Placement Error Measurements Using Digital Portal and Simulation Image Correlations," Med. Phys. 20 (3), pp. 679–685, 1993.

Meertens et al., "A Method for the Measurement of Field Placement Errors in Digital Portal Images," Phys. Med. Biol., vol. 35, No. 3, pp. 299–323, 1990.

Michalski et al., "Prospective Clinical Evaluation of an Electronic Portal Imaging Device," Int. J. Radiation Oncology Biol. Phys., vol. 34, No. 4, pp. 843–951, 1996.

Mitchie et al., "Computation and Analysis of Image Motion: A Synopsis of Current Problems and Methods," International Journal of Computer Vision, 19 (1), pp. 29–55, 1996.

Mori et al., "Accurate Contiguous Sections without Breath–Holding on Chest CT: Value of Respiratory Gating and Ultrafast CT," AJR:162, pp. 10571062, May 1994.

Moseley et al., "A Semiautomatic Method for Registration of Portal Images," Med. Phys. 21 (4), pp. 551–558, Apr. 1994.

Munro et al., "A Digital Fluoroscopic Imaging Device for Radiotheraphy Localization," Int. J. Radiation Oncology Biol. Phys., vol. 18, pp. 641–649, 1990.

Munro, P., "Portal Imaging Technology: Past, Present, and Future," Seminars in Radiation Oncology, vol. 5, No. 2, pp. 115–133, Apr. 1995.

Murray et al., "Motion Tracking with an Active Camera," IEEE Transactions on Pattern Analysis and Machine Intelligence, vol. 16, No. 5, pp. 449–459, May 1994.

Nie et al., "Development of a Computerized Portal Verification Scheme for Pelvic Treatment Fields," Int. J. Radiation Oncology Biol. Phys., vol. 36, No. 1, Supplement, p. 205, 1996 (Abstract).

Ohara et al., "Irradiation Synchronized with Respiration Gate," Int. J. Radiation Oncology Biol. Phys., vol. 17, pp. 853–857, 1989.

O'Malley et al., "Kinematic Analysis of Human Walking Gait Using Digital Image Processing," Med. & Biol. Eng. & Computing, vol. 31, pp. 392–398, 1993.

Peltola, S., "Gated Radiotherapy to Compensate for Patient Breathing," Proceedings of the 11th Varian Users Meeting, Marco Island, Florida, 3 pages, 1986.

Pisanaky et al., "Correlation of Pretherapy Prostate Cancer Characteristics with Seminal Vesicle Invasion in Radical Prostatectomy Specimens," Int. J. Radiation Oncology Biol. Phys., vol. 36, No. 3, pp. 585–591, 1996.

Post et al., "Three–Dimensional Respiratory–Gated MR Angiography of Coronary Arteries: Comparison with Conventional Coronary Angiography," AJR: 166, 1399–1404, Jun. 1996.

Richardson, R., "A Low–Cost Simulator for Testing the Respiratory Gating Function of the Brattle Physiological Synchronizer," J. Nucl. Med., vol. 21, pp. 574–575, 1980.

Ritchie et al., "Predictive Respiratory Gating: A New Method to Reduce Motion Artifacts on CT Scans," Radiology, vol. 190, pp. 847–852, 1994.

Rudat et al., "Combined Error of Patient Positioning Variability and Prostate Motion Uncertainly in 3D Conformal Radiotherapy of Localized Prostate Cancer," Int. J. Radiation Oncology Biol. Phys., vol. 35, No. 5, pp. 1027–1034, 1998.

Runge et al., "Respiratory Gating in Magnetic Resonance Imaging at 0.5 Tesla," Radiology 151: 521–523, 1984.

Saw et al., "Dose Volume Assessment of High Dose Rate $^{192}$IR Endobronchial Implants," Int. J. Radiation Oncology Biol. Phys., vol. 34, No. 4, pp. 917–922, 1996.

Shalev et al., "Video Techniques for On–Line Portal Imaging," Computerized Medical Imaging and Graphics, vol. 13, No. 3, pp. 217–226, 1989.

Sherouse et al., "Computation of Digitally Reconstructed Radiographs for Use in Radiotherapy Treatment Design," Int. J. Radiation Oncology Biol. Phys., vol. 18, pp. 651–658, 1990.

Sibley et al., "The Treatment of Stage III Nonsmall Cell Lung Cancer Using High Dose Conformal Radiotherapy," Int. J. Radiation Oncology Biol. Phys., vol. 33, No. 5, pp. 1001–1007, 1995.

Swarnakar et al., "Accurate Patient Repositioning for Fractionated Radiosurgery," Int. J. Radiation Oncology Biol. Phys., vol. 36, Issue 1, Supplement, 1996, (Abstract).

Szeliski et al., "Spline–Based Image Registration," International Journal of Computer Vision 22 (3), pp. 199–218, 1997.

Uenohara et al., "Vision–Based Object Registration for Real–Time Image Overlay," Comput. Biol. Med., vol. 25, No. 2, pp. 249–260, 1995.

van den Elsen et al., "Medical Image Matching—A Review with Classification," IEEE Engineering in Medicine and Biology, pp. 26–39, Mar. 1993.

van Geuns, et al., "Magnetic Resonance Imaging of the Coronary Arteries: Clinical Results from Three Dimensional Evaluation of a Respiratory Gated Technique," Heart 82, pp. 515–519, 1999.

van Herk et al., "A Comprehensive System for the Analysis of Portal Images," Radiotherapy and Oncology 29, pp. 221–229, 1993.

van Herk et al., "A Matrix Ionisation Chamber Imaging Device for On–Line Patient Setup Verification During Radiotherapy," Radiotherapy and Oncology, 11, pp. 369–376, 1988.

van Herk et al., "Automatic Three–Dimensional Correlation of CT–CT, CT–MRI, and CT–SPECT Using Chamfer Matching," Med. Phys. 21 (7), pp. 1163–1178, 1994.

van Herk, M., "Development and Clinical Application of Three–Dimensional Image Correlation Algorithms with Emphasis on Application in Radiotherapy," Cancer Treatment Radiotherapy, p. 201, 1994, (Abstract).

Vannier, M., "Respiratory Gating by Impedance Plethysmography," The Journal of Nuclear Medicine, vol. 25, No. 10, pp. 1142–1143, 1984.

Wang et al., "A Robust Morphological Algorithm for Automatic Radiation Field Extraction and Correlation of Portal Images," Med. Phys. 21 (2), pp. 237–244, Feb. 1994.

Wang et al., "Navigator–Echo–Based Real–Time Respiratory Gating and Triggering for Reduction of Respiration Effects in Three–Dimensional Coronary MR Angiography," Radiology 198, pp. 55–60, 1996.

Weber et al., "Correlative Image Registration," Seminars in Nuclear Medicine, vol. XXIV, No. 4, pp. 311–323, Oct. 1994.

Weinhous, M., "Treatment Verification Using a Computer Workstation," Int. J. Radiation Oncology Biol. Phys., vol. 19, pp. 1549–1554, 1990.

Wells et al., "Multi–Model Volume Registration by Maximization of Mutual Information," Medical Image Analysis, vol. 1, No. 1, pp. 35–51, 1996.

Westbrook et al. "Quality Assurance in Daily Treatment Procedure: Patient Movement During Tangential Fields Treatment," Radiotherapy and Oncology, 22, pp. 299–303, 1991.

Willoughby et al., "Evaluation and Scoring of Radiotherapy Treatment Plans Using an Artificial Neural Network," Int. J. Radiation Oncology Biol. Phys., vol. 34, No. 4, pp. 923–930, 1996.

Wong et al., "On–Line Radiotherapy Imaging with an Array of Fiber–Optic Image Reducers," Int. J. Radiation Oncology Biol. Phys., vol. 18, pp. 1477–1484, 1990.

Wong et al., "The Cumulative Verification Image Analysis Tool for Offline Evaluation of Portal Images," Int. J. Radiation Oncology Biol. Phys., vol. 33, No. 5, pp. 1301–1310, 1995.

Wood et al., "Suppression of Respiratory Motion Artifacts in Magnetic Resonance Imaging," Med. Phys. 13(6), pp. 794–805, Nov./Dec. 1986.

Yan et al., "A New Model for 'Accept or Reject' Strategies in Off–Line and On–Line Megavoltage Treatment Evaluation," Int. J. Radiation Oncology Biol. Phys., vol. 31, No. 4, pp. 943–952, 1995.

Yan et al., "The Use of Adaptive Radiation Therapy to Reduce Setup Error: A Prospective Clinical Study," Int. J. Radiation Oncology Biol. Phys., vol. 36, No. 1, Supplement, p. 204, 1996, (Abstract).

Allard et al., "Three–Dimensional Analysis of Human Movement", Human Kinetics, Chapters 1–7, 1995, 148 pgs.

Balter et al., "Automated Localization of the Prostate at the Time of Treatment Using Implanted Radiopaque Markers: Technical Feasibility," Int. J. Radiation Oncology Biol. Phys., vol. 33, No. 5, 1995, pp. 1281–1286.

Bijhold, "Evaluation of Treatment Setup in Radiotherapy Using an Electronic Portal Imaging Device" 1992, 158 pgs.

Borghese et al., "An Algorithm for 3–D Automatic Movement Detection by Means of Standard TV Cameras," IEEE Trans. Biomed. Eng. BME, vol. 37, Dec. 1990, pp. 1221–1225.

Burt et al., "Local Correlation Measures for Motion Analysis: A Comparative Study," IEEE Conf. Pattern Recognition Image Processing, 1982, pp. 269–274.

Cox et al., "Positioning Accuracy of the Neurotron 1000," Proceedings of the 37th Annual ASTRO Meeting, 1995, p. 301.

ELITE: Motion Analyser Brochure, 1995, 6 pgs.

El–Hakim, "A Hierarchical Approach to Stereo Vision," Photogrammetric Engineering and Remote Sensing, 55(4), Apr. 1989, pp. 443–448.

El–Hakim et al., "The VCM Automated 3–D Measurement System—Theory, Application, and Performance Evaluation," Applications of Artificial Intelligence X: Machine Vision and Robotics, Proc.SPIE 1708, 1992, pp. 460–482.

El–Hakim et al., "Multicamera Vision Based Approach to Flexible Feature Measurement for Inspection and Reverse Engineering," Optical Engineering, vol. 32, No. 9, Sep. 1993, 15 pgs.

Ferrigno et al., "ELITE: A Digital Dedicated Hardware System for Movement Analysis Via Real–Time TV Signal Processing," IEEE Transactions on Biomedical Engineering, vol. BME–32, No. 11, Nov. 1985, pp. 943–950.

Ferrigno et al., "Pattern Recognition in 3–D Automatic Human Motion Analysis," ISPRS Journal of Photogrammetry, Remote Sensing 45, 1990, pp. 227–247.

Fitts, "Precision Correlation Tracking Via Optimal Weighting Functions," 18th IEEE Conference on Decision and Control, 1979, pp. 280–283.

Friedman, "Detection of Signals by Template Matching," Baltimore: Johns Hopkins Press, 1969, 65 pgs.

Frohlich et al., "A Simple Device for Breath–Level Monitoring During CT," Radiology 156, 1985, 235 pgs.

Gilhuijs, "Automated Verification of Radiation Treatment Geometry" Amsterdam 1995, 169 pgs.

Goshtasby et al., "A Two–Stage Cross–Correlation Approach to Template Matching," IEEE Trans. Pattern Analysis and Machine Intelligence, vol. PAMI–6, No. 3, May 1984, pp. 374–378.

Haralick et al., "Computer and Robot Vision", Addison–Wesley Publishing Co., 1992, pp. 326–355.

Inada et al., "Proton Irradiation Synchronized with Respiratory Cycle," Proton Medical Research Center, University of Tsukuba, vol. 52, No. 8, Aug. 1992, pp. 1161–1167.

Jones, "A Respiration Monitor for Use with CT Body Scanning and Other Imaging Techniques," British Journal of Radiology, vol. 55, Jul. 1982, pp. 530–534.

Kanade et al., "CMU Strategic Computing Vision Project Report: 1984–1985", The Robotics Institute Carnegie–Mellon University, Nov. 1985, 45 pgs.

Kanade et al., 1998 Year End Report Autonomous Planetary Rover at Carnegie Mellon, The Robotics Institute Carnegie Mellon University, Jan. 1989, 93 pgs.

Kanazawa et al., "Beam Deceleration in the Operation of the Beam Extraction with a Patient Respiration," EPAC, 1996, 3 pgs.

Meertens, "On–Line Acquisition and Analysis of Portal Images," Amsterdam 1989, 157 pgs.

Milliken et al., "Performance Characteristics of a Video–Image–Substraction–Based Patient Positioning System," 1996, p. 203 (Abstract).

Murphy et al., "The Accuracy of Dose Localization for an Image–Guided Frameles Radiosurgery System," Medical Physics vol. 23, No. 12, Dec. 1996, pp. 2043–2049.

Murphy et al., "Frameless Radiosurgery Using Real–Time Image Correlation for Beam Targeting," Med Phys vol. 23, No. 6, Jun.1996, pp. 2 pgs.

Nakajima, et al., "Timing of Synchronization in Intermittent Irradiation Synchronized with Respiratory Motion," J Jpn. Soc. Ther. Radiol. Oncol , vol. 7, 1995, pp. 351–356.

Noda, K., et al., "Performance of a Respiration–Gated Beam Control System for Patient Treatment," EPAC96 Contributions to the Proceedings, 1996, 3 pgs.

Noda et al., "Beam Test on Ring Property in HIMAC Synchrotron," EPAC, 1994, pp. 982–984.

Noda et al., "Slow Beam Extraction by a Traverse RF Field with AM and FM," Nuclear Instruments and Methods in Physics Research A, vol. 374, 1996, pp. 269–277.

Noda et al., "A Treatment Beam Control System for Irradiation Gated by Respiration of a Patient," JAERI–Conf, 1995, pp. 439–441.

Okumura et al., "Respiration–Gate Irradiation System for Proton Radiotherapy," Proceedings of the 11th International Conference of the use of Computers in Radiation Therapy, 1994, pp. 358–359.

Okutomi et al., "A Locally Adaptive Window for Signal Matching," International Journal of Computer Vision, vol. 7, No. 2, 1992, pp. 143–162.

Otsu "A Threshold Selection Method from Gray–Level Histograms," IEEE Transactions on Systems, Man, and Cybernetics, vol. 9 1979, pp. 62–66.

Papanikolopoulos et al., "Visual Tracking of a Moving Target by a Camera Mounted on a Robot: A Combination of Control and Vision," IEEE Transactions on Robotics and Automation, vol. 9, No. 1, Feb. 1993, pp. 14–35.

Pedotti et al., "OptoElectronic–Based System," Three Dimensional Analysis of Human Movement, Human Kinetics, Chapter 4, 1995, pp. 57–77.

Peltola, "A 3–d Body Contour Device for Radiotherapy Planning," Proceedings Symposium 'Varian in Medicine', May 30, 1985, pp. 6–11.

Pilgrim, "Two Dimensional Image Matching and Difference Detection," Aust. J. Geod. Photogram. Surv., vol. 56, Jun. 1992, pp. 1–36.

Preising et al., "Robotic Stereotaxic Radiosurgery," 14th International Conf., IEEE Eng Med Bio, Paris, France, Oct. 1992, pp. 1057–1058.

Rehg et al., "Model–Based Tracking of Self–Occluding Articulated Objects," Proceedings of the 5th International Conference on Computer Vision, Cambridge, MA, Jun. 20–23, 1995, pp. 612–617.

Suit, et al., "Potential for Improvement in Radiation Therapy," International J. Radiation Oncology Biology Physics, vol. 14, 1988, pp. 777–786.

Sumi et al., "Three–level Broad–edge Template Matching and its Application to Real–Time Vision System," IEICE Trans Inf System, vol. E78–D, No. 12, 1995, pp. 1526–1532.

Takada et al., "Status Report of HIMAC Accelerator Facility," EPAC, Dec. 1996, 3 pgs.

Ten Haken, et al., "Potential Benefits of Gating Conformal Irradiation of Liver Tumors to the Ventilatory Cycle," Proceedings of the 37th Annual ASTRO Meeting, 1995, p. 187.

Thorpe et al., "1986 Year End Report for Road Following at Carnegie Mellon," Technical Report CMU–RI–TR–87–11, Robotics Institute, Carnegie Mellon University, May 1987, pp. 1–60.

Thorpe et al., "1988 Year End Report for Road Following at Carnegie Mellon," Technical Report CMU–RI–TR–89–5, The Robotics Institute, Carnegie Mellon University, 1989, pp. 1–124.

van Herk, "An Electronic Portal Imaging Device: Physics, Development and Application," 1992, pp. 1–164.

van Herk et al. "Quantification of Organ Motion During Conformal Radiotherapy of the Prostate by Three Dimensional Image Registration," Int. J. Radiat. Oncol. Biol. Phys., vol. 33, 1995, pp. 1311–1320.

Van den Heuvel et al., "Clinical Implementation of an Objective Computer–aided Protocol for Intervention in Intra–treatment Correction using Electronic Portal Imaging," Radiotherapy & Oncology, vol. 35, No. 3, Jun. 1995, pp. 232–239.

Verhey, "Immobilizing and Positioning Patients for Radiotherapy," Seminars in Radiation Oncology, Volumes, No. 2, Apr. 1995, pp. 100–114.

Willett et al., "Effect of the Respiratory Cycle on Mediastinal and Lung Dimensions in Hodgkin's Disease. Implications for Radiotherapy Gated to Respiration," Cancer 60, No. 6, 1987, pp. 1232–1237.

Yamada et al., "Present Status of the Medical Accelerator HIMAC," JAERI–Conference, 1995, pp. 5–7.

Young et al., "Neural Network Object Recognition for Inspection of Patient Setup in Radiation Therapy Using Portal Images," Department of Radiation Medicine, IEEE, 1996, pp. 3418–3421.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 2 was previously cancelled.
Claims 21-28 are cancelled.
Claims 1 and 3-20 were not reexamined.

* * * * *